US012624149B2

(12) United States Patent
Pai et al.

(10) Patent No.: US 12,624,149 B2
(45) Date of Patent: May 12, 2026

(54) POLYTHIOL COMPOSITION AND OPTICAL COMPOSITION COMPRISING SAME

(71) Applicant: SK pucore co., ltd., Ulsan (KR)

(72) Inventors: Jae Young Pai, Gyeonggi-do (KR); Jeong Moo Kim, Gyeonggi-do (KR); Hyuk Hee Han, Gyeonggi-do (KR); Jung Hwan Myung, Gyeonggi-do (KR); Kyeong Hwan You, Gyeonggi-do (KR)

(73) Assignee: SK PUCORE CO., LTD., Ulsan (KR)

( * ) Notice: Subject to any disclaimer, the term of this patent is extended or adjusted under 35 U.S.C. 154(b) by 470 days.

(21) Appl. No.: 18/044,379

(22) PCT Filed: Sep. 7, 2021

(86) PCT No.: PCT/KR2021/012122

§ 371 (c)(1),
(2) Date: Mar. 8, 2023

(87) PCT Pub. No.: WO2022/055221

PCT Pub. Date: Mar. 17, 2022

(65) Prior Publication Data

US 2023/0357484 A1 Nov. 9, 2023

(30) Foreign Application Priority Data

Sep. 10, 2020 (KR) ........................ 10-2020-0116308

(51) Int. Cl.

| | |
|---|---|
| ***C07C 321/04*** | (2006.01) |
| ***C07C 315/04*** | (2006.01) |
| ***C07C 321/14*** | (2006.01) |
| ***C08G 18/38*** | (2006.01) |
| ***C08G 18/76*** | (2006.01) |
| ***G02B 1/04*** | (2006.01) |

(52) U.S. Cl.

CPC ........ *C08G 18/3868* (2013.01); *C07C 315/04* (2013.01); *C07C 321/04* (2013.01); *C07C 321/14* (2013.01); *C08G 18/38* (2013.01); *C08G 18/7642* (2013.01); *G02B 1/041* (2013.01)

(58) Field of Classification Search

CPC ... C07C 321/04; C07C 321/14; C07C 315/04; C08G 18/38; C08G 18/3876; G02B 1/041

See application file for complete search history.

(56) References Cited

U.S. PATENT DOCUMENTS

| | | | |
|---|---|---|---|
| 5,352,758 A | 10/1994 | Kanemura et al. | |
| 2009/0082544 A1 | 3/2009 | Kuma et al. | |
| 2018/0297943 A1 | 10/2018 | Kageyama et al. | |
| 2019/0218331 A1 | 7/2019 | Kousaka et al. | |
| 2020/0031986 A1 | 1/2020 | Kim | |

FOREIGN PATENT DOCUMENTS

| | | | | |
|---|---|---|---|---|
| EP | 0742244 A2 | 11/1996 | |
| EP | 2824126 A1 | 1/2015 | |
| JP | WO2018/003059 A1 | 1/2018 | |
| JP | 2018-058922 A | 4/2018 | |
| KR | 10-2011-0021371 A | 3/2011 | |
| KR | 10-1338568 B1 | 12/2013 | |
| KR | 10-2014-0142375 A | 12/2014 | |
| KR | 10-2018-0024561 A | 3/2018 | |
| KR | 10-2019-0106721 A | 9/2019 | |
| TW | 201811742 A | 4/2018 | |
| WO | WO-2013069965 A1 * | 5/2013 | ........... C08G 18/722 |
| WO | WO-2017095119 A1 * | 6/2017 | ............... G02B 1/04 |

OTHER PUBLICATIONS

WO-2013069965-A1_May 16, 2013_English Translation.*

WO-2017095119-A1_Jun. 8, 2017_English Translation.*

International Search Report for the International Application No. PCT/KR2021/012122 issued by the Korean Patent Office on Dec. 14, 2021.

Office Action on the Chinese Patent Application No. 202180061853.4 issued by the Chinese Patent Office on Sep. 20, 2023.

Partial supplementary European Search Report for European Patent Application No. 21867087.5 issued by the European Patent Office on Sep. 5, 2024.

Notice of Allowance for Korean Patent Application No. 10-2020-0116308 issued by the Korean Patent Office on Mar. 4, 2026.

* cited by examiner

*Primary Examiner* — Michael L Leonard
(74) *Attorney, Agent, or Firm* — IP & T GROUP LLP

(57) ABSTRACT

A polythiol composition according to exemplary embodiments includes at least two different polythiol-based compounds, wherein a peak area (%) of the polythiol compound represented by C8H18S6, which is measured through a high performance liquid chromatographic (HPLC) analysis graph obtained at a wavelength of 230 nm, ranges from 0.90% to 1.30%. By controlling the sub-polythiol compound, an optical product having excellent transmittance and optical properties can be manufactured.

12 Claims, 4 Drawing Sheets

POLYTHIOL COMPOSITION AND OPTICAL COMPOSITION COMPRISING SAME

This application is a national stage application of PCT/KR2021/012122 filed on Sep. 7, 2021, which claims priority to Korean Patent Application No. 10-2020-0116308 filed on Sep. 10, 2020. The disclosure of each of the foregoing applications is incorporated herein by reference in its entirety.

BACKGROUND

1. Field

The present invention relates to a polythiol composition and an optical composition including the same. More particularly, the present inventions relates to a polythiol composition including polythiol-based compounds different from each other, and an optical composition including the same.

2. Description of the Related Art

A polythiol compound is widely used, for example, as a raw material for manufacturing a polyurethane resin. For example, a polythiol compound is used to manufacture an optical lens using a polyurethane resin, and quality such as purity of the polythiol compound as a raw material may directly influence on the quality of the optical lens.

For example, a polythiourethane-based compound prepared by reacting a polythiol compound and an isocyanate compound may be used as a base material of the optical lens.

For example, Korean Patent Laid-Open Publication No. 10-1338568 discloses a method for synthesizing a polythiol compound by reacting a polyol compound with thiourea to prepare an isothiouronium salt, and then hydrolyzing it using aqueous ammonia.

Depending on the number of functional groups, a chain length, etc. of the synthesized polythiol compound, optical properties such as a transparency, refractive index, etc. of the lens may be finely modified. Accordingly, in order to reliably implement an optical lens with desired optical properties, it may necessary to finely control the constitutional composition of a polythiol compound.

SUMMARY

An object according to exemplary embodiments is to provide a polythiol composition with improved reaction properties and optical properties, as well as a method for preparation thereof.

An object according to exemplary embodiments is to provide an optical composition including a polythiol composition with improved reaction properties and optical properties.

An object according to exemplary embodiments is to provide an optical product manufactured using the optical composition described above.

A polythiol composition according to exemplary embodiments includes: at least two different polythiol-based compounds, wherein a peak area (%) of the polythiol compound represented by $C_8H_{18}S_6$, which is measured through a high performance liquid chromatographic (HPLC) analysis graph obtained at a wavelength of 230 nm, may range from 0.90% to 1.30%.

In some embodiments, the polythiol compound represented by $C_8H_{18}S_6$, may have a structure of Formula 2 below:

[Formula 2]

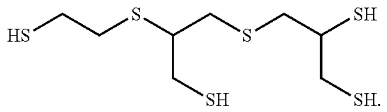

In some embodiments, the polythiol-based compound may include a sub-polythiol compound represented by Formula 2 above, and a main polythiol compound having a higher molecular weight than that of the sub-polythiol compound.

In some embodiments, the main polythiol compound may include a tetrafunctional polythiol compound having a larger number of carbon atoms than that of the sub-polythiol compound.

In some embodiments, the main polythiol compound may include at least one selected from tetrafunctional polythiol compounds represented by Formulae 1-1 to 1-3 below:

[Formula 1-1]

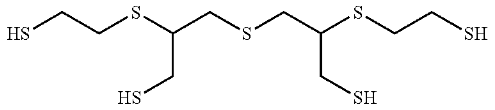

[Formula 1-2]

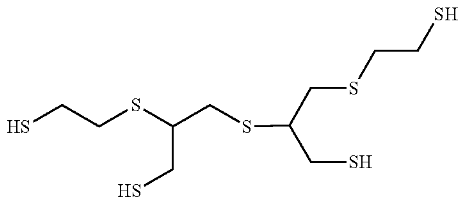

[Formula 1-3]

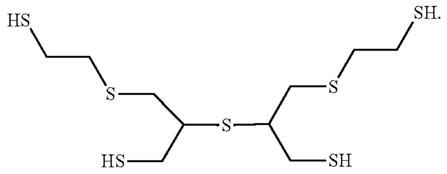

In some embodiments, a Reaction rate Control Index defined by Equation 1 below may range from 0.006 to 0.017:

$$\text{Reaction rate Control Index: RCI}=A/B \qquad \text{[Equation 1]}$$

(in Equation 1, A represents a peak area (%) of the polythiol compound represented by $C_8H_{18}S_6$, which is measured through the HPLC analysis graph, and B represents a peak area (%) of the polythiol compound represented by each of Formulae 1-1 to 1-3, which is measured through the HPLC analysis graph).

In some embodiments, a peak area of each of the polythiol compounds represented by Formulae 1-1 to 1-3, which is measured through the HPLC analysis graph, may range from 78.6% to 85%.

According to a method for preparing a polythiol composition in exemplary embodiments, a metal sulfide may be introduced into a preliminary polyol compound to generate a polyol intermediate. Subsequently, a sub-polythiol compound formation promoter may be added to the polyol intermediate. Then, the polyol intermediate may be converted into a polythiol-based compound through thiolation.

In some embodiments, the polythiol composition may include at least two different polythiol-based compounds, wherein a peak area (%) of the polythiol compound represented by $C_8H_{18}S_6$, which is measured through a high performance liquid chromatographic (HPLC) analysis graph obtained at a wavelength of 230 nm, may range from 0.90% to 1.30%.

In some embodiments, the preliminary polyol compound may be synthesized by a reaction of 2-mercaptoethanol and epihalohydrin, wherein the polythiol compound formation promoter in the polyol intermediate may be added in a predetermined equivalent range to 2-mercaptoethanol so as to satisfy the range of a peak area (%) of the polythiol compound.

In some embodiments, the sub-polythiol compound formation promoter may include glycidol.

An optical composition according to exemplary embodiments may include a polythiol composition and an isocyanate-based compound. The polythiol composition may include at least two different polythiol-based compounds, wherein a peak area (%) of the polythiol compound represented by $C_8H_{18}S_6$, which is measured through a high performance liquid chromatographic (HPLC) analysis graph obtained at a wavelength of 230 nm, ranges from 0.90% to 1.30%.

According to exemplary embodiments, there is provided an optical product including a polythiourethane resin prepared from the above optical and polymerizable composition.

According to the above embodiments, the polythiol composition of the exemplary embodiments may include at least two different tetrafunctional polythiol-based compounds, and may include a sub-polythiol compound having a predetermined structure in a predetermined content range measured through HPLC.

The sub-polythiol compound may have a relatively shorter chain length, reduce coloration of a lens, and control a reaction rate with an isocyanate-based compound, whereby an optical lens having desired refractive index may be obtained with high reliability.

DETAILED DESCRIPTION OF THE EMBODIMENTS

Figure 1:
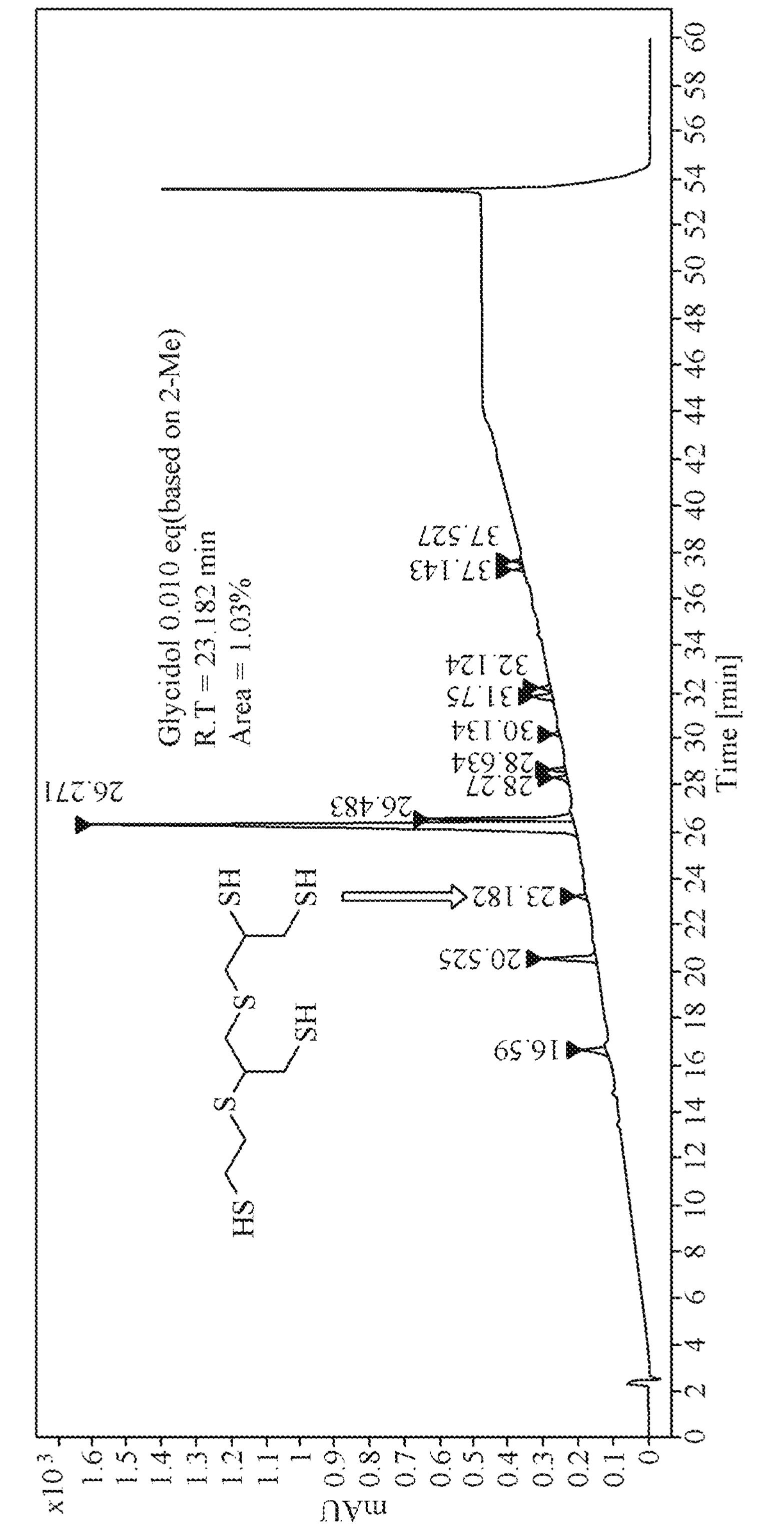
FIGS. 1 to 4 are images showing high performance liquid chromatography (HPLC) analysis graphs of polythiol compositions prepared according to examples and comparative examples.

Hereinafter, embodiments of the present application will be described in detail. In this regard, the present invention may be altered in various ways and have various embodiments, such that specific embodiments will be illustrated in the drawings and described in detail in the present disclosure. However, the present invention is not limited to the specific embodiments, and it will be understood by those skilled in the art that the present invention is to cover all modifications, equivalents, and alternatives falling within the spirit and scope of the present invention.

Unless otherwise defined, all terms including technical and scientific terms used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

According to one aspect of the present application, there is provided a polythiol composition including polythiol-based compounds.

According to exemplary embodiments, the polythiol composition may include at least two different polythiol-based compounds. In some embodiments, the polythiol composition may include at least two tetrafunctional polythiol compounds.

For example, the polythiol composition may include a main polythiol compound and a sub-polythiol compound.

Non-limited examples of the main polythiol compound may include compounds represented by Formulae 1-1 to 1-3 below. For example, the main polythiol compound may include at least one of compounds represented by Formulae 1-1 to 1-3 below:

[Formula 1-1]

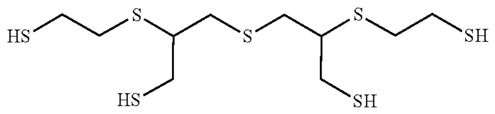

[Formula 1-2]

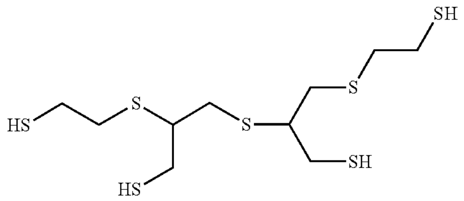

[Formula 1-3]

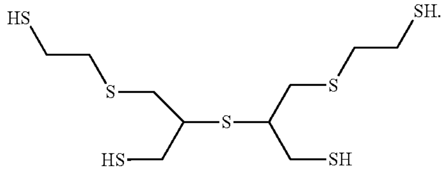

In a preferred embodiment, the main polythiol compound may include a tetrafunctional polythiol compound represented by Formula 1-1.

The sub-polythiol compound may include a tetrafunctional polythiol compound which has a shorter chain length, a smaller molecular weight or a small number of carbon atoms than those of the main polythiol compound.

According to exemplary embodiments, the sub-polythiol compound may be represented by $C_8H_{18}S_6$. In some embodiments, the sub-polythiol compound may include a compound represented by Formula 2 below:

[Formula 2]

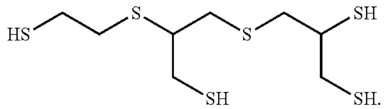

As described above, the sub-polythiol compound may have a shorter chain length and/or a smaller molecular weight than those of the main polythiol compound. The sub-polythiol compound may be provided as a regulator of polymerization ("polymerization regulator") with an isocyanate-based compound to be described below.

For example, if a reaction rate between the main polythiol compound and the isocyanate-based compound is excessively increased, it may cause inhomogeneity ("stria") of an optical product such as a lens. On the other hand, if a reaction rate between the main polythiol compound and the isocyanate-based compound is excessively decreased, it may cause white turbidity/coloration of the optical product, hence reducing a transmittance thereof.

According to exemplary embodiments, as the sub-polythiol compound is included in a proper amount, a desirable reaction rate between the main polythiol compound and the isocyanate-based compound may be maintained. Further, an entire thiol value and a liquid refractive index of the polythiol composition may be finely controlled by the sub-polythiol compound.

Thereby, an optical product such as a lens capable of having uniform optical properties and inhibited coloration and stria phenomena may be obtained using the polythiol composition. Further, it is possible to improve chemical stability of the polythiol composition or the optical product, such that a white turbidity phenomenon of the lens may be efficiently inhibited.

When an amount of the sub-polythiol compound is excessively increased, as a low-molecular weight thiol component is increased, the reaction rate may be excessively increased. On the other hand, when the amount of the sub-polythiol compound is excessively decreased, functions of the above-described reaction rate regulator may not be sufficiently implemented, and coloration of the optical product and/or a decrease in transmittance may occur.

According to exemplary embodiments, a content (e.g., peak area %) of the sub-polythiol compound, which is measured with a peak area of the sub-polythiol compound through a high performance liquid chromatographic (HPLC) analysis graph obtained at a wavelength of 230 nm, may range from 0.90% to 1.30%.

Within the above range, the control of reaction rate and coloration/stria inhibitory effects may be sufficiently implemented.

In a preferred embodiment, a content of the sub-polythiol compound measured through HPLC may range from 0.95% to 1.30%, preferably 1.0% to 1.30%, and more preferably 1.03% to 1.26% or 1.05% to 1.26%.

In some embodiments, a reaction rate between the polythiol composition and the isocyanate-based compound (see Mathematical Equation 1 in the experimental example) may be maintained by the sub-polythiol compound in a range of 0.18 to 0.25, preferably 0.18 to 0.22, and more preferably 0.20 to 0.22.

Within the above range of the reaction rate, a lens with improved transmittance may be obtained while inhibiting a generation of stria due to excessive increase in reaction rate.

In some embodiments, a Reaction rate Control Index (RCI) of the polythiol composition, which is represented by Formula 1 below, may range from 0.006 to 0.017:

$$\text{Reaction rate Control Index (RCI)}=A/B \quad \text{[Equation 1]}$$

In Equation 1, A represents a content of the sub-polythiol compound, which is measured with a peak area of the sub-polythiol compound through the HPLC analysis graph, and B represents a content of the main polythiol compound, which is measured with a peak area of the main polythiol compound through the HPLC analysis graph.

The Reaction rate Control Index (RCI) may reflect a content ratio of low molecular polythiol and high molecular polythiol participating in a polymerization reaction with an isocyanate-based compound.

For example, the sub-polythiol compound may correspond to the low molecular polythiol, which has a relatively shorter molecular length and may serve as a component to increase a reaction rate with the isocyanate-based compound. On the other hand, the main polythiol compound may have a relatively higher molecular weight or molecular length and may provide a reduced reaction rate as compared to the sub-polythiol compound.

Therefore, according to the exemplary embodiments, the Reaction rate Control Index in Equation 1 may be controlled to a proper range from a unit of the polythiol composition. Accordingly, it is possible to obtain high-reliability optical products while inhibiting a generation of stria due to an excessive increase in reaction rate, as well as a reduction in transmittance, yield due to the excessive reduction in reaction rate or the like.

In some embodiments, the Reaction rate Control Index may range from 0.007 to 0.017, preferably 0.01 to 0.017, and more preferably 0.012 to 0.016.

In some embodiments, the content (e.g., peak area %) of the main polythiol compound measured through the HPLC analysis graph may range from 78.6% to 85%. For example, the HPLC peak area or content may correspond to the compounds represented by Formulae 1-1 to 1-3 above.

In a preferred embodiment, the content of the main polythiol compound measured through HPLC may range from 78.6% to 84.1%, 79.0% to 84.0%, and more preferably 81.0% to 83.25%.

Within the above range of content of the main polythiol compound, it is possible to easily secure sufficient efficiency and yield of the polymerization reaction between the polythiol compound and the isocyanate. Further, it is possible to improve the purity of the polythiol composition in an appropriate range and enhance the transmittance of the lens.

In some embodiments, the polythiol composition has a thiol value (SHV) of about 96 g/eq to 97 g/eq. Preferably, the SHV ranges from 96.1 g/eq to 96.8 g/eq.

SHV may be measured as a value obtained by dividing the sample weight by the consumed iodine equivalent when titrating a polythiol composition sample using a 0.1N iodine standard solution.

In some embodiments, a liquid refractive index of the polythiol composition may be about 1.6455 to 1.647. Preferably, the liquid refractive index is about 1.6455 to 1.6468, and more preferably 1.6455 to 1.646.

The liquid refractive index may be measured at 25° C. using a liquid refractometer.

In some embodiments, a gel permeation chromatography (GPC) purity of the polythiol composition may be 79% or more. For example, the GPC of the polythiol composition may be 79% to 88%. Preferably, the GPC purity ranges from 80% to 88%, and more preferably 81% to 85%.

According to one aspect of the present application, there is provided a method for preparing a polythiol composition including polythiol-based compounds. As described above, the polythiol composition may include at least two different tetrafunctional polythiol compounds.

A method for preparing a polythiol composition according to exemplary embodiments may include at least one of the steps, processes or actions described as S10, S20, S30 and S40 below. It should be understood that the following terms "S10, S20, S30 and S40" are used to distinguish processes for the convenience of description and are not intended to limit the sequential order thereof. For example, some or all of the processes of S10, S20, S30 and S40 below may be sequentially conducted, and/or may be conducted with altered order according to process conditions.

S10) Introducing a metal sulfide to a preliminary polyol compound to produce a polyol intermediate.

S20) Adding a sub-polythiol compound formation promoter to the polyol intermediate.

S30) Reacting the polyol intermediate with thiourea under acidic conditions to produce an isothiouronium salt.

S40) Converting the isothiouronium salt into a polythiol-based compound.

For example, in step S10, the polyol intermediate may be produced by reacting the preliminary polyol compound with the metal sulfide.

In one embodiment, the preliminary polyol compound may be obtained through a reaction with 2-mercaptoethanol and epihalohydrin as exemplified in Scheme 1 below.

[Scheme 1]

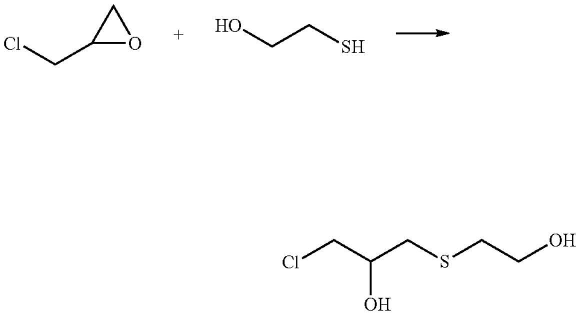

A basic catalyst may be used to promote the reaction of 2-mercaptoethanol and epihalohydrin. Examples of the basic catalyst may include tertiary amines such as triethyl amine, quaternary ammonium salts, triphenylphosphine, and trivalent chromium-based compounds. Epichlorohydrin may be used as epihalohydrin as illustrated in Scheme 1.

The obtained preliminary polyol compound may be, for example, a diol compound containing a sulfide bond.

A reaction temperature for generating the preliminary polyol compound may be, for example, −10° C. to 40° C., preferably −5° C. to 30° C., 0° C. to 25° C., and more preferably 5° C. to 20° C.

For example, a content of 2-mercaptoethanol may be 0.5 mol to 3 moles, preferably 0.7 mol to 2 moles, and more preferably 0.9 mol to 1.1 moles, based on 1 mole of epihalohydrin. The basic catalyst may be used in an amount of 0.001 mol to 0.1 mol, 0.005 mol to 0.03 mol, and more preferably 0.007 mol to 0.015 mol, based on 1 mol of epihalohydrin.

By introducing a metal sulfide to the diol compound having a sulfide bond obtained as described above, a polyol intermediate may be formed, as illustrated in Scheme 2 below.

[Scheme 2]

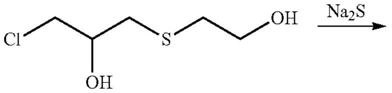

-continued

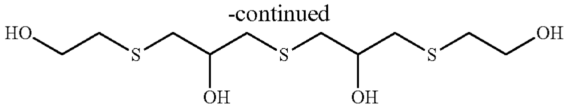

As illustrated in Scheme 2, the diol compounds may be further reacted with each other through the metal sulfide to obtain a polyol intermediate including a tetrafunctional polyol compound.

The metal sulfide may include alkali metal sulfide, and in one embodiment, as shown in Scheme 2, $Na_2S$ may be used.

For example, in step S20, a sub-polythiol compound formation promoter may be added to the polyol intermediate. In one embodiment, after addition of the metal sulfide, the sub-polythiol compound formation promoter may further be added thereto. In one embodiment, the metal sulfide and the sub-polythiol compound formation promoter may be substantially added together or simultaneously.

In some embodiments, as the sub-polythiol compound formation promoter, glycidol may be used. Glycidol may act as a nucleophile unlike epihalohydrin functioning as an electrophile. Thereby, for example, an additive reaction such as $S_N2$ reaction or $S_N1$ reaction may be inhibited in step S30. Therefore, it may lead to production of a sub-polythiol compound having a relatively small molecular weight.

The sub-polythiol compound formation promoter may be added in an amount so as to satisfy a HPLC measured content range of the above-described sub-polythiol compound. In one embodiment, the sub-polythiol compound formation promoter may be adjusted in a range of 0.005 equivalent ("eq") to 0.02 eq, 0.005 eq to 0.018 eq, and preferably 0.008 eq to 0.015 eq based on 2-mercaptoethanol.

Since the sub-polythiol compound formation promoter is added within the above range, a proper amount of the sub-polythiol compound may be added to the polythiol composition. Thereby, all of the stria phenomenon due to the excessively increased reaction rate, coloration due to the excessively decreased reaction rate, white turbidity, etc. may be effectively inhibited.

For example, in step S30, the polyol intermediate may be reacted with thiourea. As a result, according to exemplary embodiments, an isothiouronium salt may be obtained.

Acidic condition reflux may be used in the production of isothiouronium salts. In order to form the acidic conditions, acidic compounds such as hydrochloric acid, hydrobromic acid, iodic acid, sulfuric acid, phosphoric acid, and the like may be used.

The reflux temperature may be 90° C. to 120° C., and preferably 100° C. to 120° C., while the reflux time may be 1 hours to 10 hours.

For example, in step S40, the isothiouronium salt may be converted into a polythiol-based compound. According to exemplary embodiments, the isothiouronium salt may be hydrolyzed under basic conditions to produce a polythiol-based compound.

Steps S30 and S40 described above may include thiolation exemplified by Scheme 3 below.

[Scheme 3]

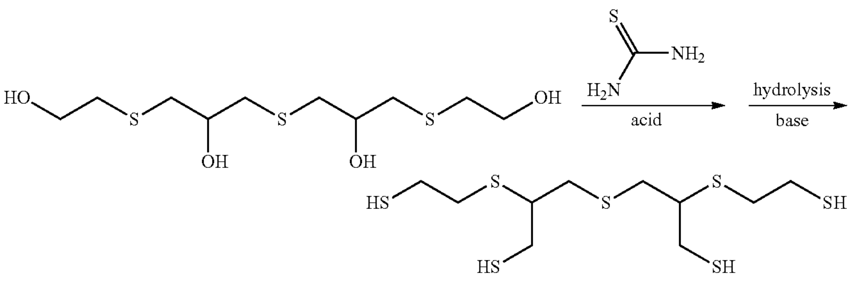

For example, it may be hydrolyzed by adding a basic aqueous solution to a reaction solution containing the isothiouronium salt. The basic aqueous solution may include alkali-metal hydroxide and/or alkaline earth metal hydroxide, such as NaOH, KOH, LiOH, $Ca(OH)_2$, etc.

In one embodiment, the reaction solution containing the isothiouronium salt is cooled to a temperature of 20° C. to 60° C., preferably 25° C. to 55° C., and more preferably 25° C. to 50° C. Thereafter, the basic aqueous solution may be added.

In one embodiment, an organic solvent may be added before adding the basic aqueous solution. An organic solvent having low reactivity or substantially no reactivity and a boiling point exceeding a thiolation reaction temperature may be used so as to allow a thiolation reaction to proceed stably.

Examples of the organic solvent may include toluene, xylene, chlorobenzene, and dichlorobenzene. Preferably, toluene may be used in consideration of reaction stability and toxicity from an organic solvent.

The polythiol-based compound obtained as described above may be further purified. For example, by repeatedly performing acid washing and water washing processes, impurities included in the polythiol-based compound may be removed, in addition, the transparency of the optical material prepared from the polythiol composition may be improved. Thereafter, drying, filtration, etc. may be additionally performed.

In one embodiment, an aqueous layer may be separated or removed through layer separation after proceeding with the hydrolysis. Acid washing may be carried out at a temperature of about 20° C. to 50° C., and preferably about 30° C. to 40° C. for 20 minutes to 1 hour, or 20 minutes to 40 minutes by introducing an acid solution (e.g., concentrated hydrochloric acid) to the obtained organic phase solution.

After the acid washing, a water washing process may be conducted by adding degassed water having a dissolved oxygen concentration adjusted to 5 ppm or less, preferably 3 ppm or less, and more preferably 2 ppm or less. The water washing process may be conducted at a temperature of about 20° C. to 50° C., preferably about 35° C. to 45° C. for 20 minutes to 1 hour, or 20 minutes to 40 minutes. The water washing process may be repeated two or more times, for example, may be conducted 3 to 6 times.

After the acid washing and water washing process, the residual organic solvent and moisture may be removed by heating under reduced pressure, followed by filtering through a filter to obtain a polythiol-based compound with high purity.

In some embodiments, a residual moisture content of the polythiol-based compound or polythiol composition may be 1,000 ppm or less, preferably in a range of 100 ppm to 500 ppm, and more preferably 150 ppm to 400 ppm.

In some embodiments, a purity of the polythiol-based compound measured through HPLC may range from 75% to 88%. Preferably, the purity ranges from 76% to 85%, and more preferably 80 to 85%.

Within the above-described ranges of moisture content and purity, polymerization efficiency may be sufficiently improved while not excessively increasing a process load, and a side reaction may be inhibited.

According to one aspect of the present application, there is provided an optical composition including the polythiol composition or polythiol-based compound.

In some embodiments, the optical composition may be a polymerizable composition including the polythiol composition and an isocyanate-based compound.

The isocyanate-based compound may include a compound which is useable as a monomer for synthesizing polythiourethane. In a preferred embodiment, the isocyanate-based compound may include 1,3-bis(isocyanatomethyl)cyclohexane, hexamethylene diisocyanate, isophorone diisocyanate, xylene diisocyanate, toluene diisocyanate and the like. These may be used alone or in combination of two or more thereof.

The optical composition such as a polymerizable composition for an optical material may further include additives such as a release agent, a reaction catalyst, a thermal stabilizer, an ultraviolet absorber, a bluing agent and the like.

Examples of the release agent may include a fluorine-based nonionic surfactant having a perfluoroalkyl group, a hydroxyalkyl group or a phosphoric acid ester group; a silicone-based nonionic surfactant having a dimethylpolysiloxane group, a hydroxyalkyl group or a phosphoric acid ester group; alkyl quaternary ammonium salts such as trimethylcetyl ammonium salt, trimethylstearyl, dimethylethylcetyl ammonium salt, triethyldodecyl ammonium salt, trioctylmethyl ammonium salt and diethylcyclohexadodecyl ammonium salt; acidic phosphoric acid ester and the like. These may be used alone or in combination of two or more thereof.

As the reaction catalyst, a catalyst used in the polymerization reaction of the polythiourethane resin may be used. For example, dialkyltin halide catalysts, such as dibutyltin dichloride and dimethyltin dichloride; dialkyltin dicarboxylate catalysts such as dimethyltin diacetate, dibutyltin dioctanoate, and dibutyltin dilaurate; dialkyltin dialkoxide catalysts such as dibutyltin dibutoxide and dioctyltin dibutoxide; dialkyltin dithio alkoxide catalysts such as dibutyltin di(thiobutoxide); dialkyltin oxide catalysts such as di(2-ethylhexyl)tin oxide, dioctyltin oxide, and bis(butoxydibutyltin)

oxide; dialkyltin sulfide catalysts, and the like may be used. These may be used alone or in combination of two or more thereof.

As examples of the ultraviolet absorber, benzophenone-based, benzotriazole-based, salicylate-based, cyanoacrylate-based, oxanilide-based compounds, and the like may be used. As examples of the thermal stabilizer, metal fatty acid salt-based, phosphorus-based, lead-based, organotin-based compounds, and the like may be used. These may be used alone or in combination of two or more thereof.

The bluing agent may be included as a color control agent of the optical material prepared from the polythiourethane resin. For example, the bluing agent may have an absorption band in a wavelength band from orange to yellow in a visible light region.

Examples of the bluing agent may include a dye, a fluorescent whitening agent, a fluorescent pigment, an inorganic pigment, and the like, and may be appropriately selected according to physical properties or resin color required for the optical product to be manufactured. When a dye is used as the bluing agent, for example, a dye having a maximum absorption wavelength of 520 nm to 600 nm, and preferably 540 nm to 580 nm may be used. Preferably, anthraquinone-based dyes may be used.

A polythiourethane resin may be produced through a polymerization reaction of the polythiol-based compound included in the polythiol composition with the isocyanate-based compound.

In some embodiments, based on a total weight of the optical composition, the polythiol-based composition or polythiol-based compound may be included in a content of about 40 to 60% by weight ("wt. %"), and the isocyanate-based compound may be included in a content of about 40 wt. % to 60 wt. %, while the additive may be included in a content of about 0.01 wt. % to 1 wt. %.

In some embodiments, a reaction rate of the optical composition included in Mathematical Equation 1 described below may be maintained in a range of 0.18 to 0.25, preferably 0.18 to 0.22 by the above sub-polythiol compound.

According to one aspect of the present application, an optical product manufactured through the above-described optical composition may be provided.

For example, after degassing the optical composition under reduced pressure, the resultant composition may be injected into a mold for molding an optical material. Mold injection may be performed, for example, in a temperature range of 20° C. to 40° C., and preferably 20° C. to 35° C.

After the mold injection, the temperature may be gradually increased, thereby allowing a polymerization reaction of the polythiourethane resin to proceed. The polymerization temperature may range from 20° C. to 150° C., and preferably 25° C. to 125° C. For example, the maximum polymerization temperature may range from 100° C. to 150° C., preferably 110° C. to 140° C., and more preferably 115° C. to 130° C.

The temperature increase rate may be 1° C./min to 10° C./min, preferably 3° C./min to 8° C./min, and more preferably 4° C./min to 7° C./min. The polymerization time may be 10 hours to 20 hours, and preferably 15 hours to 20 hours.

For example, a lens having uniform optical properties and mechanical properties can be easily obtained by appropriately controlling the reaction rate within the above temperature range.

After completion of polymerization, the polymerized polythiourethane resin may be separated from the mold to obtain an optical product. In one embodiment, after separation from the mold, a curing process may be further conducted. The curing process may be conducted in a range of 100° C. to 150° C., preferably 110° C. to 140° C., and more preferably 115° C. to 130° C. for about 1 hours to 10 hours, preferably 2 hours to 8 hours, and more preferably 3 hours to 6 hours.

The optical product may be manufactured in the form of a spectacle lens, a camera lens, a light emitting diode, etc. according to a shape of the mold.

The refractive index of the optical product may be adjusted according to the type and/or content ratio of the polythiol-based compound and the isocyanate-based compound used in the optical composition. For example, the refractive index of the optical product may be adjusted in a range of 1.56 to 1.78, 1.58 to 1.76, 1.60 to 1.78, or 1.60 to 1.76, and preferably in a range of 1.65 to 1.75 or 1.69 to 1.75.

The optical product may be improved by further conducting surface treatment such as anti-fouling, color imparting, hard coat, surface polishing, hardness strengthening and the like.

According to the above-described embodiments, a sub-polythiol compound having HPLC content in the above-described range may be included in the polythiol composition. Accordingly, an optical product with inhibited optical failures such as coloration, stria, etc. while maintaining an appropriate range of polymerization reaction can be obtained from the polythiol-based composition.

Hereinafter, embodiments provided in the present application will be further described with reference to specific experimental examples. However, the following experimental examples only illustrate the present invention and are not intended to limit the appended claims, and those skilled in the art will obviously understand that various alterations and modifications are possible within the scope and spirit of the present invention. Such alterations and modifications are duly included in the appended claims.

Example 1

1) Synthesis of Tetrafunctional Polythiol-Based Compound

After introducing 60.0 parts by weight ("wt. parts") of water, 0.3 wt. parts of triethylamine and 73.0 wt. parts of 2-mercaptoethanol (2-ME) into a reactor, a temperature of the reactor was decreased to 0° C., and 88.2 wt. parts of epichlorohydrin (ECH) was slowly added dropwise at a temperature of 15° C. or lower, and then stirred at 30° C. for 3 hours. Following this, 148.7 wt. parts of 25% sodium sulfide solution was slowly added dropwise at 20 to 25° C., followed by further stirring for 1 hour. Subsequently, 0.56 wt. parts of glycidol (0.010 eq. based on 2-mercaptoethanol) was further added, followed by further stirring for 3 hours.

Then, 486.8 wt. parts of 36% hydrochloric acid and 177.8 wt. parts of thiourea were introduced, and stirred for 3 hours while refluxing at 110° C., such that a thiuronium chloride reaction was proceeded.

After the obtained reaction solution was cooled to 50° C., 305.6 wt. parts of toluene and 332.6 wt. parts of 50% NaOH were added, and then hydrolysis was conducted at 40 to 60° C. for 3 hours.

Then, the water layer was discarded after performing layer separation for 1 hour, and 120 wt. part of 36% hydrochloric acid was added to the obtained toluene solution, followed by acid washing once at 33 to 40° C. for 30 minutes. After acid washing, 250 wt. parts of degassed water (dissolved oxygen concentration of 2 ppm) was added, and washing was conducted 4 times for 30 minutes at 35 to 45°

C. After removing toluene and residual moisture under heating and reduced pressure, it was filtered under reduced pressure through a PTFE type membrane filter thus to obtain 140 wt. parts of a polythiol composition including the tetrafunctional polythiol compound represented by the above Formula 1 as a main polythiol compound.

2) Preparation of Optical Composition and Manufacturing of Lens

After uniformly admixing 49.0 wt. parts of the polythiol composition prepared as described above, 51.0 wt. parts of xylene diisocyanate, 0.01 wt. parts of dibutyltin chloride and 0.1 wt. parts of phosphoric acid ester release agent produced by ZELEC® UN Stepan, a defoaming process was conducted at 600 Pa for 1 hour to prepare an optical composition.

Then, the composition filtered through a 3 μm Teflon filter was injected into a molding cast provided with a glass mold and a tape. A temperature of the molding cast was slowly increased from 25° C. to 120° C. at a rate of 5° C./min, and polymerization was performed at 120° C. for 18 hours. After the polymerization was completed, the molding cast was separated, followed by further curing the product at 120° C. for 4 hours to manufacture a lens sample.

Examples 2 to 6 and Comparative Examples

Polythiol compositions and lens samples were prepared in the same manner as in Example 1, except that the added equivalent amount (eq.) of glycidol used in the synthesis of the polythiol-based compound was altered as shown in Table 1 below.

Experimental Example (1) Content Assay of Main Polythiol Compound and Sub-Polythiol Compound Through HPLC Analysis In the polythiol compositions according to each of the examples and comparative examples, a peak area % of the polythiol compound included in the composition was measured through HPLC analysis performed under the following conditions.

<HPLC Analysis Condition> i) Equipment: Agilent 1260 Infinity II ii) Column: ZORBAX Eclipse Plus C18, 5 μm 4.6×250 mm iii) Mobile phase gradient: Acetonitrile (0.1% Formic Acid):Water (0.01M Ammonium Formate)=35-100: 65-0 iv) Solvent: Acetonitrile (0.1% Formic Acid)

v) Wavelength: 230 nm vi) Flow rate: 1.0 ml/min vii) Injection amount: 20 μl viii) Sample pretreatment: sample:solvent=0.1 g:10 g Specific compounds corresponding to the peaks of the HPLC graph were identified through liquid chromatography-mass spectroscopy (LC-MS). Specific conditions for LC-MS analysis are as follows.

<LC-MS Analysis Condition>

LC Conditions i) Equipment: LC 30A System (Shimadzu)

ii) Column: YMC-Pack ODS-A 150 mm×6 mm (S-5 μm, 12 nm)

iii) Mobile phase gradient: Solvent A: water, Solvent B: Acetonitrile

A:B (60:40) 30 minutes, n (0:100) 10 minutes iv) Flow rate: 1 ml/min v) Column temperature: 40° C.

vi) Detector: PDA (190 to 800 nm)

vii) Injection Volume: 10 μL

Mass Detector i) Equipment: Q Exactive (Thermo Fisher Scientific)

ii) Ionization Method: ESI iii) Scan Range: m/z 130 to 1,950 iv) Polarity: Positive & Negative

FIGS. 1 to 4 are images showing high performance liquid chromatography (HPLC) analysis graphs of polythiol compositions prepared according to the examples and comparative examples.

Figure 2:
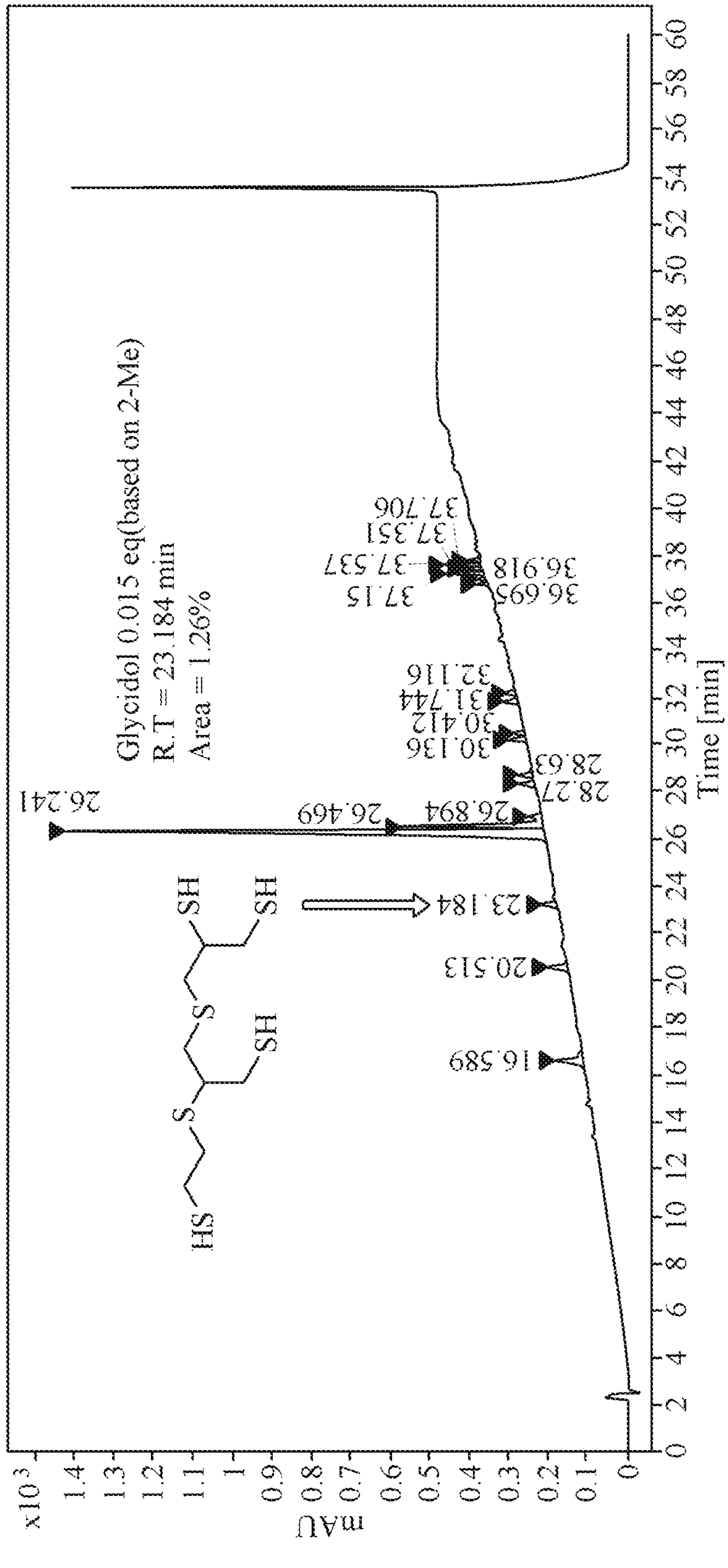
Figure 3:
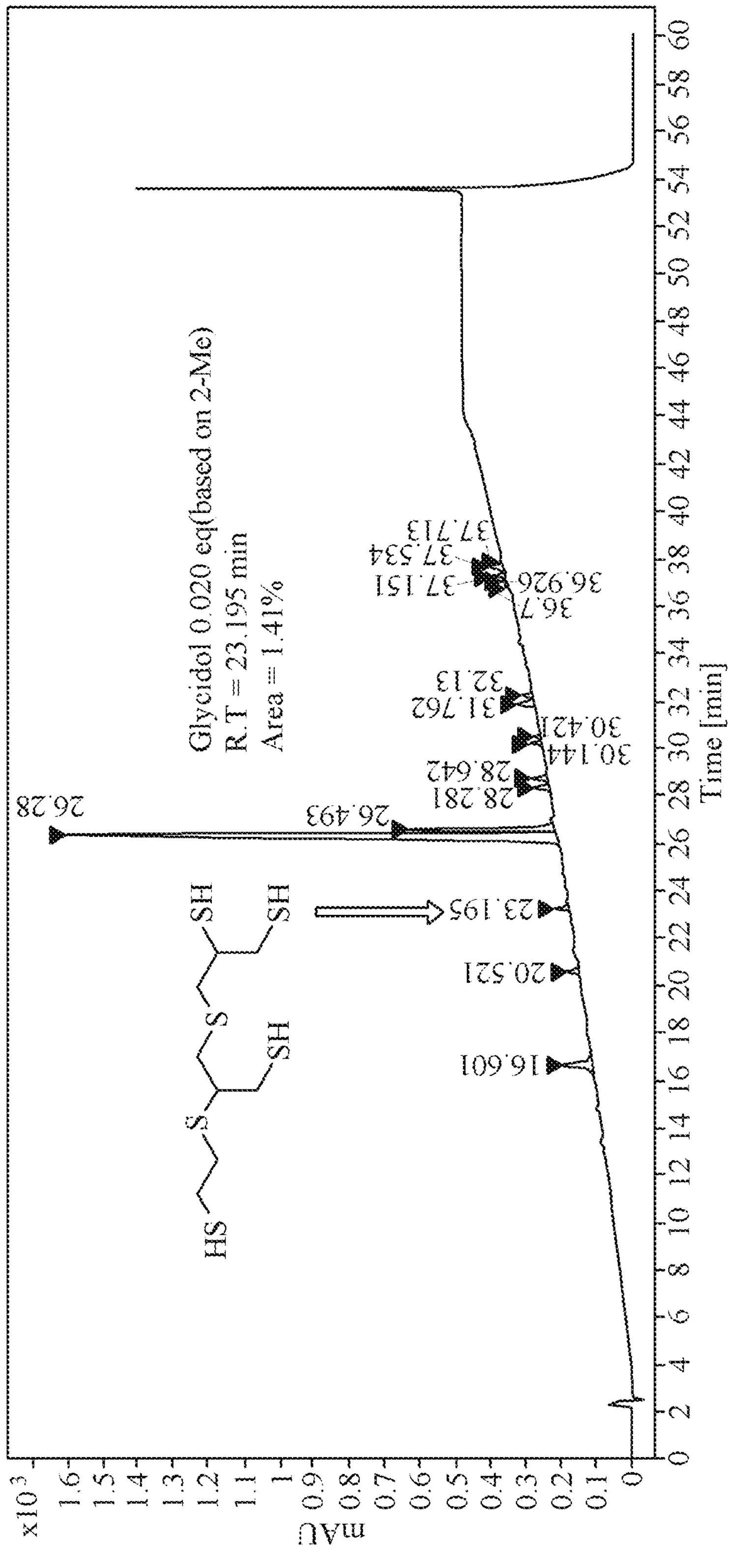
Figure 4:
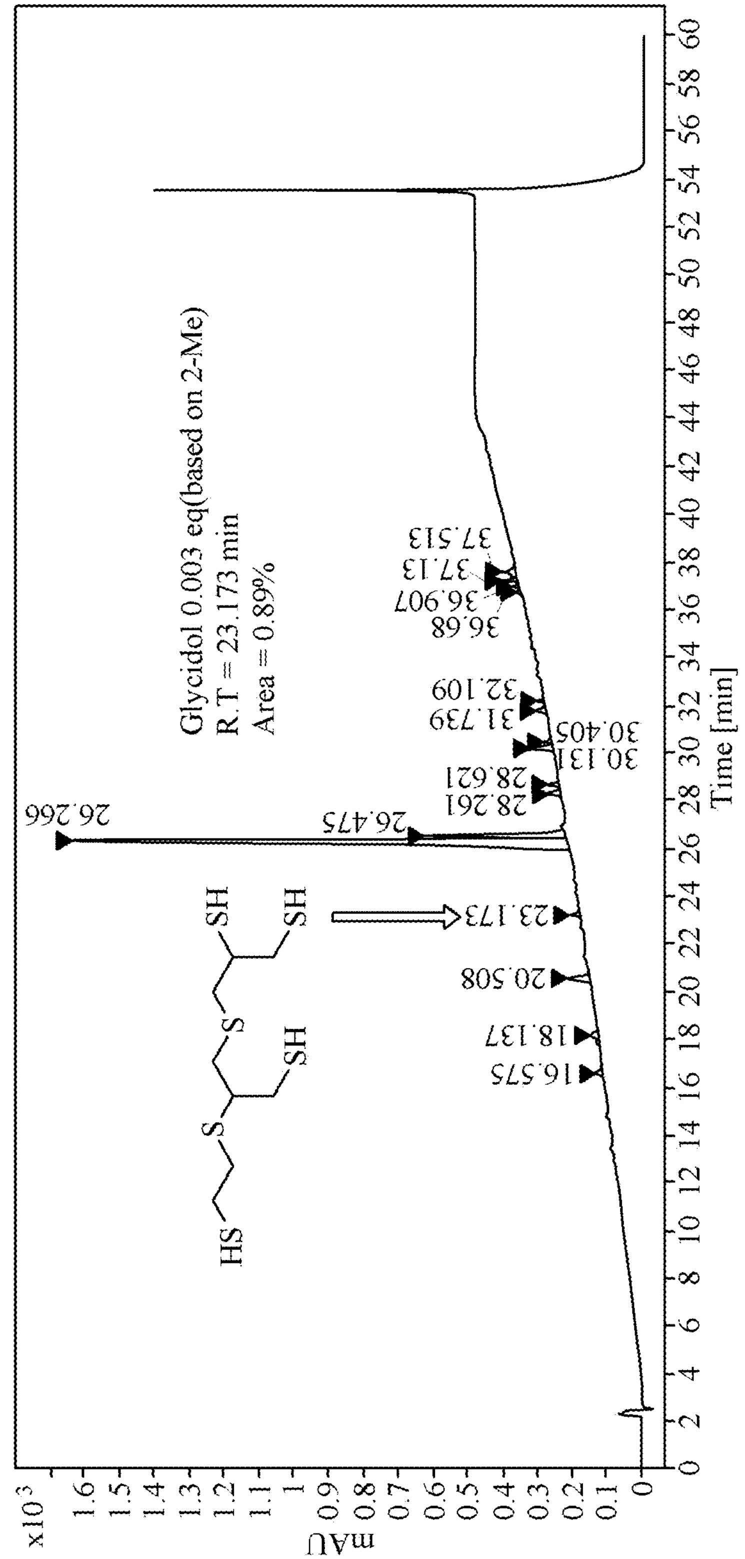

Specifically, FIGS. 1 and 2 show HPLC analysis graphs of Examples 1 and 4, respectively, while FIGS. 3 and 4 show HPLC analysis graphs of Comparative Examples 1 and 2, respectively.

(2) Evaluation of Thiol Value (SHV)

About 0.1 g of the polythiol composition prepared in each of the examples and comparative examples was introduced into a beaker, and 25 mL of chloroform was added, followed by stirring the mixture for 10 minutes. Then, 10 mL of methyl alcohol was added and stirred again for 10 minutes, and then, the resultant solution was titrated with a 0.1N iodine standard solution, followed by measuring SHV according to Equation 1 below (theoretical value: 91.7).

$$\text{SHV (g/eq.)} = \text{Sample weight (g)}/\{0.1 \times \text{Amount of iodine consumed (L)}\} \quad \text{[Equation 1]}$$

(3) Liquid Refractive Index

For the polythiol compositions synthesized in the examples and comparative examples, the refractive index at 25° C. was measured using a liquid refractometer (RA-600 (Kyoto Electronics)).

(4) GPC Purity

For the polythiol compositions synthesized in the examples and comparative examples, the purity was measured through gel chromatography analysis performed under the following conditions using an APC system (Waters).

i) Column: Acquity APC XT Column 45A (4.6*150 mm)×2 ii) Mobile phase: THF iii) Flow rate: 0.5 mL/min iv) Total driving time: 10 minutes v) Injection volume: 10 μl vi) Detector: RID 40° C.

(5) Evaluation of Stria

As described above, a lens sample having a diameter of 75 mm and −4.00D was prepared using the polymerizable composition according to each of the examples and comparative examples. A light from a mercury lamp light source was transmitted through the prepared lens sample, and the transmitted light was projected on a white plate to determine the presence or absence of stria according to the presence or absence of contrast. Standards for evaluation are as follows.

○: Stria not observed x: Stria clearly observed visually (6) Measurement of Polymerization Reaction Rate (Reactivity Slope)

Using a non-contact viscometer of EMS-1000 (KEM), the standard viscosity (Standard cps) was first confirmed with a viscosity standard solution (Brookfield, 1000 eps, 25° C.). Thereafter, the viscosity was measured at 10° C. for 24 hours for the polymerizable compositions according to the examples and comparative examples, respectively. Using the measured values, mathematical formulation ("mathematization") was conducted with an X-axis as a time and a Y-axis as a viscosity while converting the Y-axis in a logarithmic scale as shown in Mathematical Equation 1 below, and then the reaction rate was derived therefrom.

$$Y=a\times\exp(b\times X) \quad \text{[Mathematical Equation 1]}$$

In Mathematical Equation 1, 'a' value represents an initial viscosity (cps) while 'b' value represents the reaction rate, the measured value was expressed by rounding to the two decimal places of the measured value.

(5) Evaluation of Transmittance after Coloring

The sonication-washed lens sample of each of the examples and comparative examples was subjected to coloring in a coloring bath (Brown coloring solution, 10 minutes, a temperature of the coloring bath: 96 to 98° C.). The colored lens sample was washed with flowing deionized water at room temperature, followed by measuring transmittance (Measuring device: LTM-200, LED Transmittance Meter).

Measured results of physical properties of the polythiol compositions as well as measured results of physical properties of the lenses manufactured using the same, respectively, shown in Tables 1 and 2 below.

TABLE 1

| | Physical properties of polythiol composition | | | | | | |
|---|---|---|---|---|---|---|---|
| | Added eq. of glycidol based on 2-ME | SHV (g/eq.) | Liquid refractive index | Sub-polythiol HPLC area % (A) (230 nm) | Main polythiol (Formula 1-1) HPLC area % (B) (230 nm) | RCI (A/B) | GPC purity (%) |
| Example 1 | 0.010 eq. | 96.4 | 1.6462 | 1.03 | 83.14 | 0.012 | 83 |
| Example 2 | 0.008 eq. | 96.6 | 1.6465 | 0.99 | 83.25 | 0.012 | 83 |
| Example 3 | 0.012 eq. | 96.2 | 1.6458 | 1.05 | 82.43 | 0.013 | 82 |
| Example 4 | 0.015 eq. | 96.1 | 1.6457 | 1.26 | 81.09 | 0.016 | 81 |
| Example 5 | 0.005 eq. | 96.8 | 1.6468 | 0.90 | 84.01 | 0.011 | 84 |
| Example 6 | 0.007 eq. | 96.7 | 1.6466 | 0.95 | 83.25 | 0.011 | 83 |
| Example 7 | 0.018 eq. | 95.7 | 1.6455 | 1.30 | 79.22 | 0.016 | 79 |
| Comparative Example 1 | 0.020 eq. | 95.5 | 1.6453 | 1.41 | 78.57 | 0]018 | 78 |
| Comparative Example 2 | 0.003 eq. | 97.0 | 1.6468 | 0.89 | 83.33 | 0.011 | 83 |
| Comparative Example 3 | Not added | 97.2 | 1.6470 | 0.52 | 84.21 | 0.006 | 84 |

TABLE 2

| | Physical properties of lens | | |
|---|---|---|---|
| | Stria | Reaction rate | Transmittance after coloring |
| Example 1 | o | 0.20 | 68% |
| Example 2 | o | 0.18 | 67% |
| Example 3 | o | 0.21 | 69% |
| Example 4 | o | 0.22 | 72% |
| Example 5 | o | 0.17 | 67% |
| Example 6 | o | 0.17 | 67% |
| Example 7 | o | 0.23 | 78% |
| Comparative Example 1 | x | 0.26 | 80% |
| Comparative Example 2 | o | 0.17 | 64% |
| Comparative Example 3 | o | 0.16 | 63% |

Referring to Table 1 and 2, in the examples including the sub-polythiol compounds with adjusted contents according to the exemplary embodiments, it could be seen that a high-transmittance optical lens with the prevention of excessive increase in reaction rate and refractive index and reduced stria/coloration was obtained.

The invention claimed is:

1. A polythiol composition, comprising at least two different polythiol-based compounds, wherein a peak area (%) of a polythiol compound represented by $C_8H_{18}S_6$, which is measured through a high performance liquid chromatographic (HPLC) analysis graph obtained at a wavelength of 230 nm, ranges from 0.90% to 1.30%.

2. The polythiol composition according to claim 1, wherein the polythiol compound represented by $C_8H_{18}S_6$ has a structure represented by Formula 2 below:

[Formula 2]

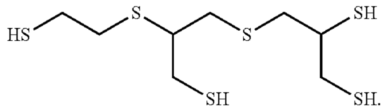

3. The polythiol composition according to claim 2, wherein the polythiol-based compound includes a sub-polythiol compound represented by Formula 2 above, and a main polythiol compound having a higher molecular weight than that of the sub-polythiol compound.

4. The polythiol composition according to claim 3, wherein the main polythiol compound includes a tetrafunctional polythiol compound having a larger number of carbon atoms than that of the sub-polythiol compound.

5. The polythiol composition according to claim 3, wherein the main polythiol compound includes at least one selected from tetrafunctional polythiol compounds represented by Formulae 1-1 to 1-3 below:

[Formula 1-1]

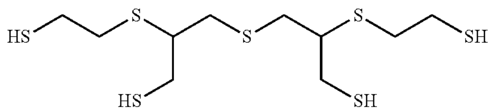

-continued

[Formula 1-2]

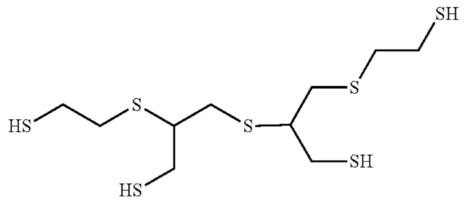

[Formula 1-3]

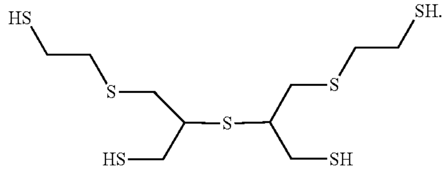

6. The polythiol composition according to claim 5, wherein a Reaction rate Control Index defined by Equation 1 below ranges from 0.006 to 0.017:

$$\text{Reaction rate Control Index}=A/B \quad \text{[Equation 1]}$$

(in Equation 1, A represents a peak area (%) of the polythiol compound represented by $C_8H_{18}S_6$, which is measured through the HPLC analysis graph, and B represents a peak area (%) of the polythiol compound represented by each of Formulae 1-1 to 1-3, which is measured through the HPLC analysis graph).

7. The polythiol composition according to claim 5, wherein the peak area of each of the polythiol compounds represented by Formulae 1-1 to 1-3, which is measured through the HPL analysis graph, ranges from 78.6% to 85%.

8. A method for preparing a polythiol composition, the method comprising:

introducing a metal sulfide to a preliminary polyol compound to generate a polyol intermediate;

adding a sub-polythiol compound formation promoter to the polyol intermediate; and converting the polyol intermediate into a polythiol-based compound through thiolation, and wherein the polythiol composition includes at least two different polythiol-based compounds, and wherein a peak area (%) of a polythiol compound represented by $C_8H_{18}S_6$ in the polythiol composition, which is measured through a high performance liquid chromatographic (HPLC) analysis graph obtained at a wavelength of 230 nm, ranges from 0.90% to 1.30%.

9. The method according to claim 8, wherein the preliminary polyol compound is synthesized by a reaction of 2-mercaptoethanol and epihalohydrin, wherein, in the step of adding the sub-polythiol compound formation promoter to the polyol intermediate, the promoter is added in a predetermined equivalent range to 2-mercaptoethanol so as to satisfy the range of a peak area (%) of the polythiol compound.

10. The method according to claim 8, wherein the sub-polythiol compound formation promoter includes glycidol.

11. An optical composition, comprising:

a polythiol composition which comprises at least two different polythiol-based compounds, wherein a peak area (%) of a polythiol compound represented by $C_8H_{18}S_6$, which is measured through a high performance liquid chromatographic (HPLC) analysis graph obtained at a wavelength of 230 nm, ranges from 0.90% to 1.30%; and an isocyanate-based compound.

12. An optical product, comprising a polythiourethane resin prepared from the optical composition according to claim 11.

* * * * *